US00PP26312P2

(12) United States Plant Patent

Lyrene et al.

(10) Patent No.: US PP26,312 P2
(45) Date of Patent: Jan. 19, 2016

(54) BLUEBERRY PLANT NAMED 'FL06-203'

(50) Latin Name: ***Vaccinium corymbosum* L.**
Varietal Denomination: FL06-203

(71) Applicant: Florida Foundation Seed Producers, Inc., Marianna, FL (US)

(72) Inventors: Paul M. Lyrene, Micanopy, FL (US); James W. Olmstead, Gainesville, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 14/544,781

(22) Filed: Feb. 12, 2015

(51) Int. Cl.
*A01H 5/08* (2006.01)

(52) U.S. Cl.
USPC ..... Plt./157

(58) Field of Classification Search
USPC ..... Plt./157
See application file for complete search history.

(56) References Cited

U.S. PATENT DOCUMENTS

PP12,165 P2 10/2001 Lyrene
PP19,341 P2 10/2008 Lyrene

OTHER PUBLICATIONS

U.S. Appl. No. 14/544,722, filed Feb. 9, 2015, Lyrene.

*Primary Examiner* — Anne Grunberg
(74) *Attorney, Agent, or Firm* — Dentons US LLP

(57) ABSTRACT

'FL06-203' is a new and distinct southern highbush blueberry (*Vaccinium corymbosum* L.) variety distinguished by a very low chilling requirement, early bloom, upright growth habit, and fruit that are firm, sweet, with a small dry picking scar.

6 Drawing Sheets

Latin name of the genus and species of the plant claimed: *Vaccinium corymbosum* L.

Variety denomination: 'FL06-203'.

BACKGROUND OF THE INVENTION

The present invention relates to a new and distinct hybrid variety of southern highbush blueberry (*Vaccinium corymbosum* L.) named 'FL06-203'. 'FL06-203' is a blueberry clone distinguished by its low chilling requirement, vigorous, upright bush, and large, sweet, firm berries that ripen from early February through late April when grown in south central Florida under evergreen conditions. Several hundred plants of 'FL06-203' have been propagated by softwood stem cuttings in Gainesville, Fla., and the resulting plants have all been phenotypically indistinguishable from the original plant. Contrast is made to 'Emerald' (U.S. Plant Pat. No. 12,165), an important variety widely planted in the southeastern United States. The claimed plant is important because it is more upright, earlier blooming, and has earlier maturing fruit than 'Emerald'. Fruit of 'FL06-203' are also sweeter, firmer, and have a small, dry picking scar when compared to 'Emerald'. 'FL06-203' has higher yields than 'Emerald' when grown as an evergreen plant.

'FL06-203' originated as a seedling from a cross between 'FL02-12' (unpatented) as the female (seed) parent and 'Farthing' (U.S. Plant Pat. No. 19,341) as the male (pollen) parent. This cross was made in a greenhouse at Gainesville, Fla., in February 2002. The seedling was planted in a high-density field nursery located in Citra, Fla., in May 2003, and the first fruit were evaluated in April 2004. After the third year of fruiting in the field, in the spring of 2006, 'FL06-203' was asexually propagated by softwood stem cuttings, and an experimental 15-plant test plot was established as part of a variety test in Windsor, Fla., in February 2007. Based on the growth, yield, and fruit quality of this plot, 'FL06-203' was repropagated by softwood stem cuttings and experimental test plots ranging from 5 to 50 plants were established near Arcadia, Citra, Interlachen, Haines City, and Windsor, Fla. These plots have been observed during flowering and ripening each year, and no mutations or off-type plants have been observed.

'FL06-203' differs from the parent 'Farthing' (U.S. Plant Pat. No. 19,341) in that 'FL06-203' has a lower chilling requirement, an earlier bloom period, a more upright growth habit, and sweeter fruit with more blue color. 'FL06-203' differs from the proprietary parent 'FL02-12' (unpatented) in that 'FL06-203' is earlier ripening and has a lower chilling requirement. 'FL06-203' differs from the commercial variety 'Emerald' (U.S. Plant Pat. No. 12,165), an important variety widely planted in the southeastern United States, in that 'FL06-203' blooms earlier and has a lower chilling requirement that allows it to be grown as an evergreen plant in regions conducive to this management system. 'FL06-203' berries ripen earlier and are sweeter than 'Emerald' berries.

SUMMARY OF THE INVENTION

Blueberry variety 'FL06-203' exhibits outstanding and distinguishing characteristics when grown under normal horticultural practices in Florida, including: (1) a low chilling requirement, particularly for the flower buds; (2) a vigorous, upright bush; (3) early ripening (50% ripe berries in North Florida around April 10, and March 1 in South Central Florida); and (4) large, sweet, firm berries with a small, dry picking scar.

BRIEF DESCRIPTION OF THE DRAWINGS

The accompanying photographs show typical bush, flower, and fruit characteristics for 'FL06-203'. Colors shown are as true as can be reasonably reproduced by photographic procedures and may differ from those cited in the detailed description, which accurately describes the colors of 'FL06-203'.

DETAILED BOTANICAL DESCRIPTION

Figure 1:
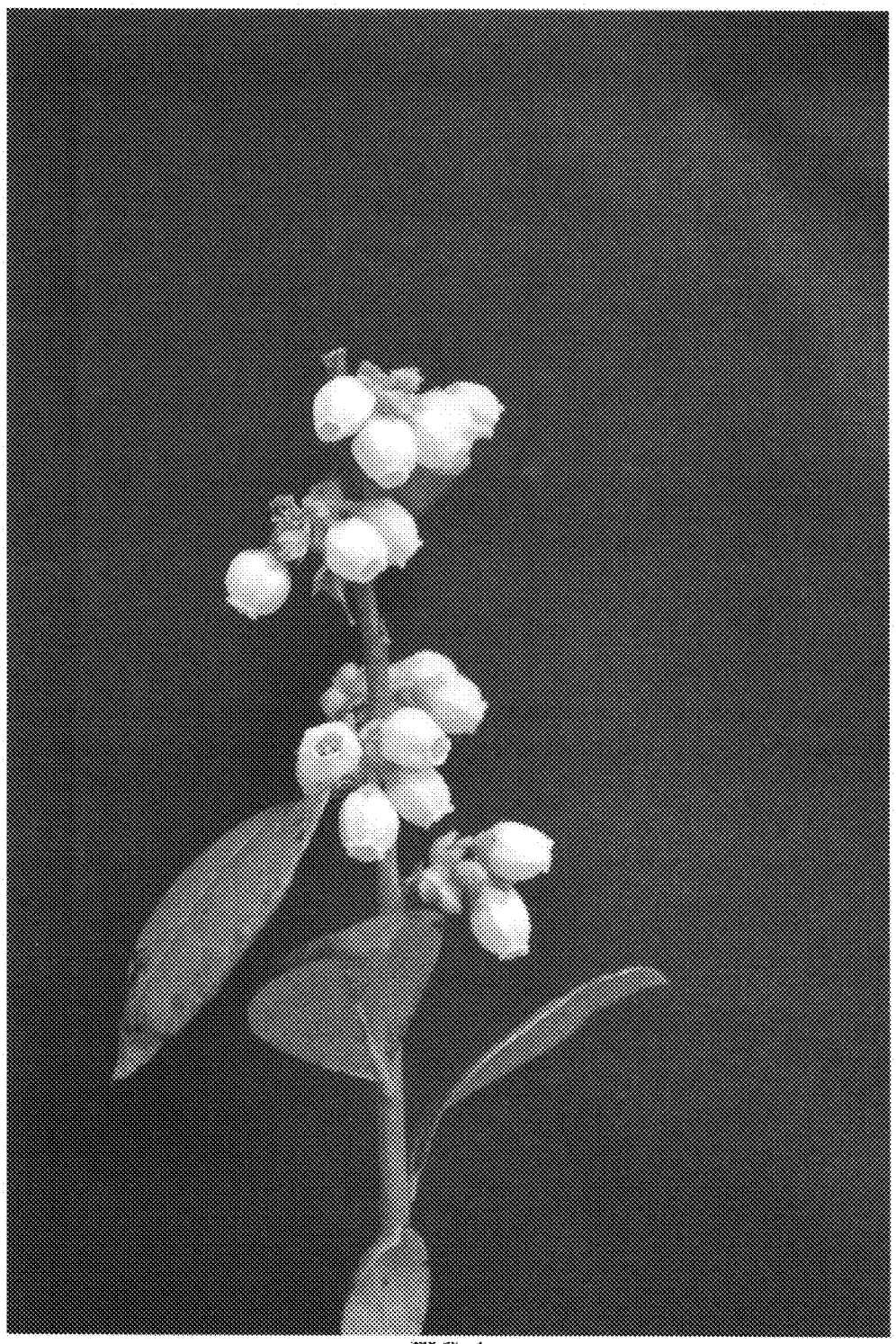
FIG. 1—Shows several clusters of opening 'FL06-203' flowers during the early stages of flowering in February.
Figure 2:
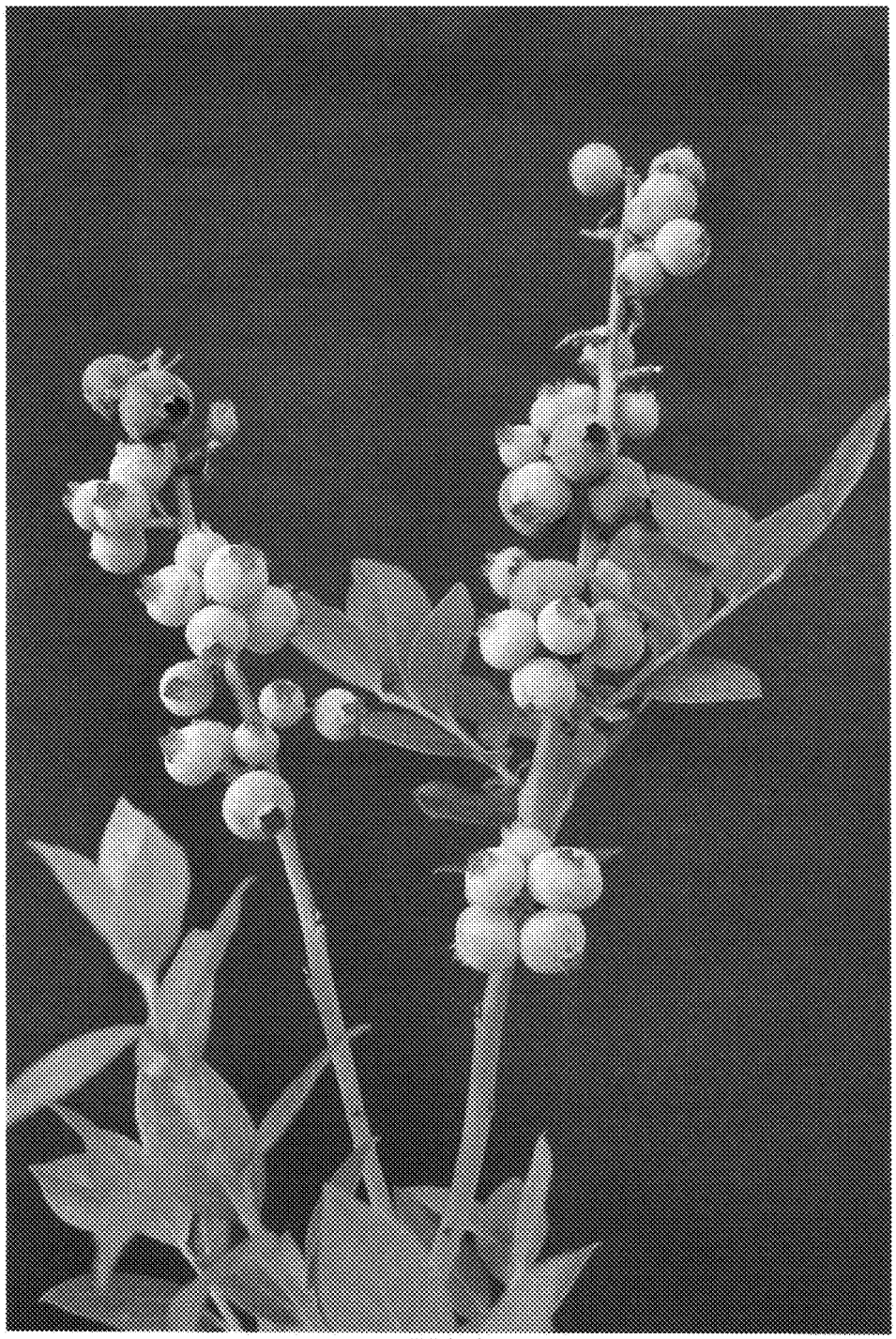
FIG. 2—Shows several clusters of 'FL06-203' berries during the fruit ripening season.
Figure 3:
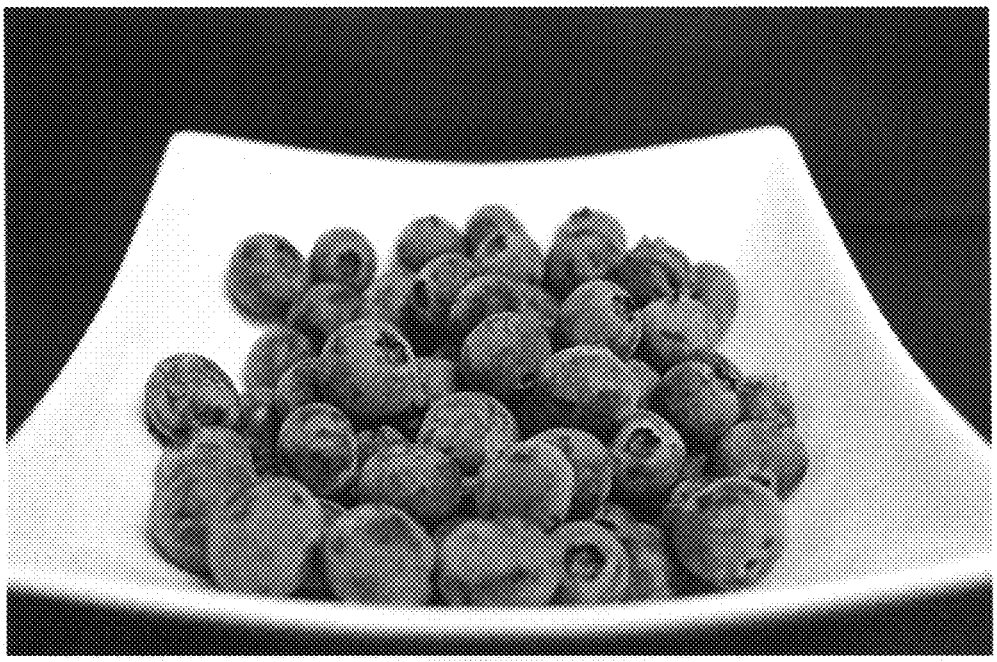
FIG. 3—Shows a close-up of harvested 'FL06-203' berries.
Figure 4:
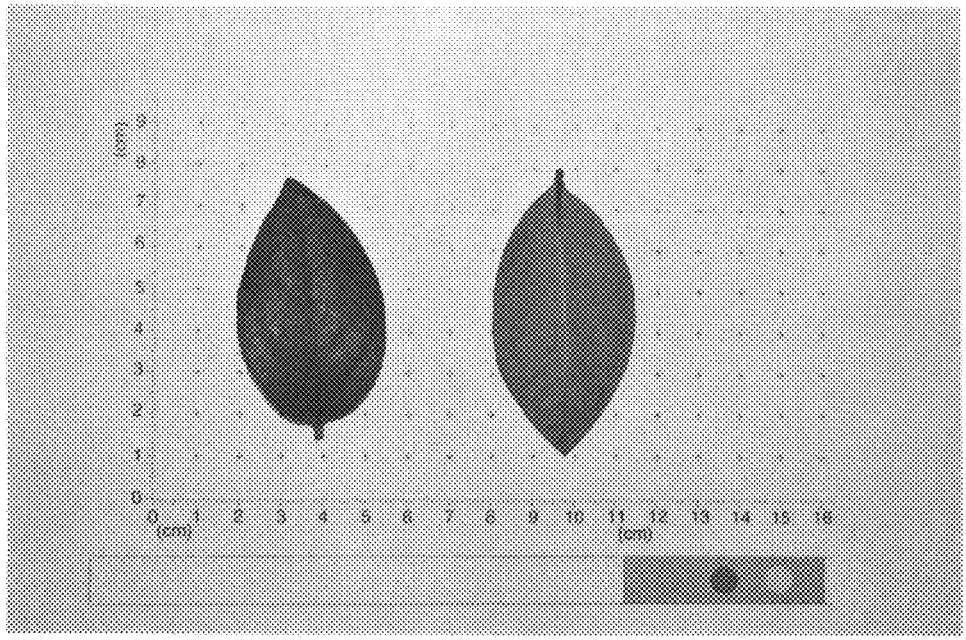
FIG. 4—Shows a close-up of mature 'FL06-203' leaves with a scale bar.
Figure 5:
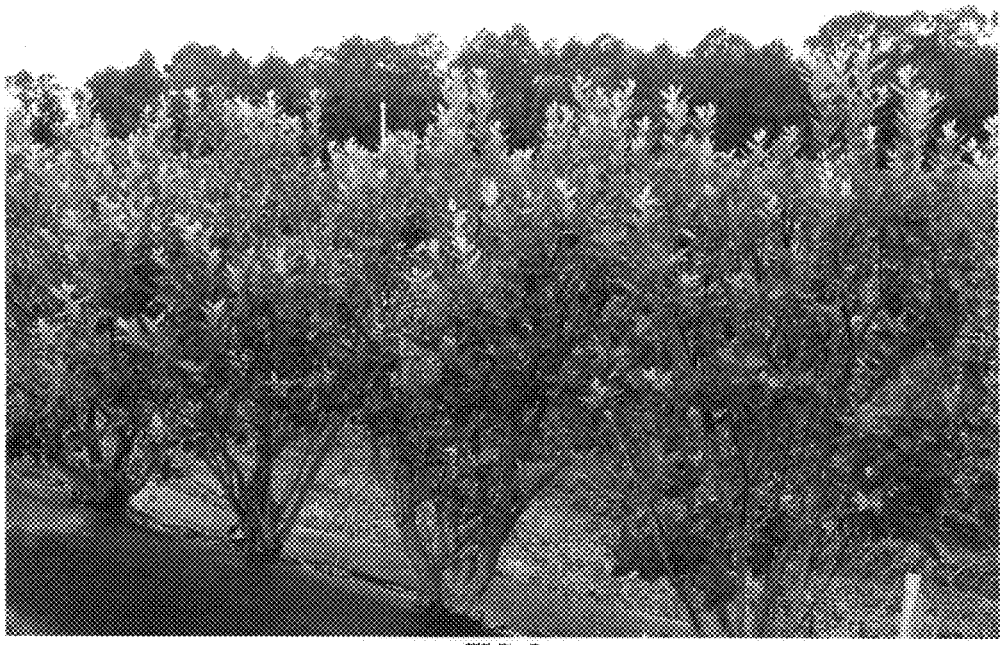
FIG. 5—Shows a group of four-year-old 'FL06-203' plants in July with the upright plant architecture visible.
Figure 6:
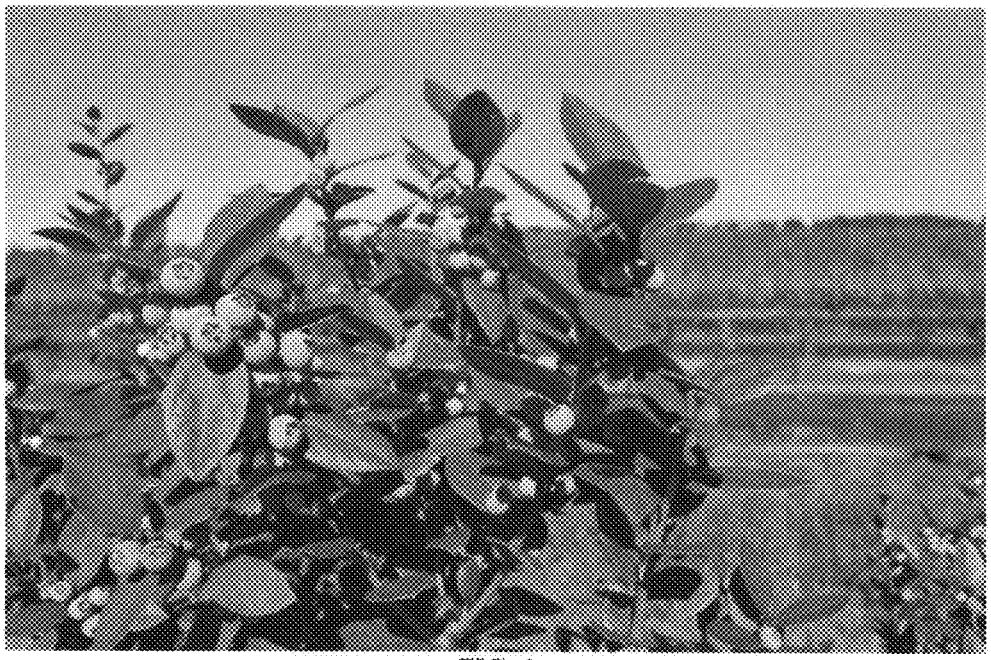
FIG. 6—Shows upright shoots of three-year-old 'FL06-203' plants with evergreen leaves and developing berries in January when grown near Arcadia, Fla.

The following detailed description sets forth the distinctive characteristics of 'FL06-203'. The data that define these characteristics were collected from asexual reproductions carried out in Florida. The plant history was taken on a plot of 50 four-year-old plants growing in a commercial field near Windsor, Fla. Certain characteristics may vary with plant age. 'FL06-203' has not been observed under all possible environmental conditions, and the measurements given may vary when grown in different environments. Where means are given, the sample size was 20. Color descriptions are based on The Royal Horticultural Society (R.H.S.) Colour Chart by The Royal Horticultural Society, London, Fifth Edition, 2007. When the R.H.S. color designations differ from the accompanying photographs, the R.H.S. color designations are accurate.

Phenotypic Description of *Vaccinium corymbosum* L. ('FL06-203')

Plant:

*Plant vigor.*—Medium. Vigor is less than 'Emerald' (U.S. Plant Pat. No. 12,165).

*Growth habit.*—Upright.

*Flower bud density (number) along flowering twigs in January.*—Medium to high.

*Twigginess.*—Medium.

*Tendency toward evergreenness.*—High.

*Productivity.*—In northeast Florida, 'FL06-203' produces 1.5 to 2.5 kg per season from plants 3 years or older. In south central Florida, 'FL06-203' produces over 4 kg per season from plants 3 years or older.

*Chilling requirement.*—Based on the forcing canes in a greenhouse, the chilling requirement of floral buds is expected to be approximately 150 hours below 7° C. when grown as a deciduous plant. When evaluated in trial sites receiving an average less than 200 hours below 7° C., 'FL06-203' has performed well.

*Cold hardiness.*—'FL06-203' has not been grown in temperate climates with extremely cold winter temperatures. Plants have survived winter freezes of −6° C. with minimal damage.

*Ease of propagation.*—'FL06-203' has only been propagated from softwood stem cuttings, where the rooting percentage has greater than 80% and is comparable to other varieties.

Trunk and branches:

*Suckering tendency.*—Low. Three-year-old plants typically have 3 to 7 major canes arising from a crown 30 cm in diameter.

*Surface texture (of strong, 6-month-old shoots observed in January).*—Smooth.

*Surface texture (of 3-year-old and older wood).*—Rough.

*Color of new twigs observed in the field.*—Yellow-green 145A.

*Color of 3-year-old, rough-textured canes.*—Greyed-brown 199D.

*Internode length (strong, upright shoots measured in January).*—Mean of 12.0 mm.

Leaves:

*Length (including petiole, from tip of petiole to end of blade).*—Mean of 6.4 cm.

*Width (at widest point).*—Mean of 3.2 cm.

*Shape.*—Elliptic, with a rounded base and acute tip.

*Margin.*—Entire.

*Color.*—Upper surface: Green 137D. Lower surface: Greyed-green 191A.

*Pubescence.*—Upper surface of leaves: Absent. Lower surface of leaves: Absent. Margins: Absent.

*Relative time of leafing versus flowering.*—When not treated with hydrogen cyanamide in mid-winter, leafing is delayed relative to flowering.

Flowers:

*Arrangement.*—Flowers are arranged alternately along a short, leafless, deciduous branch.

*Fragrance.*—Slight floral fragrance.

*Shape.*—Urceolate.

*Flowering period.*—Mean date of 50% open flowers in Citra, Fla. is January 26; averages 10 days earlier than 'Emerald'.

*Cluster (tight, medium, loose).*—Loose.

*Number of flowers per cluster.*—Mean of 4.5.

*Pedicel.*—Length at time of anthesis: Mean of 5.1 mm. Color at time of anthesis: Yellow-green 145B.

*Peduncle.*—Length at time of anthesis: Highly variable, mean of 6.7 mm. Color at time of anthesis: Yellow 4C with Greyed-red 179B on sun-exposed side.

*Calyx.*—Surface texture: Smooth. Diameter: Mean of 5.7 mm. Color: Green 137B to Green 138B on tips of calyx lobes.

*Corolla.*—Diameter: Mean of 7.3 mm. Length (from pedicel attachment point to corolla tip excluding the pedicel): Mean of 10.2 mm. Aperture diameter: Mean of 4.2 mm. Texture: Smooth. Color: Greyed-white 156D.

Reproductive organs:

*Style.*—Length (top of ovary to stigma tip): Mean of 9.4 mm. Color: Yellow-green 144D. Location of tip of stigma relative to lip of the corolla — Stigma tip is approximately even with the corolla lip.

*Anthers.*—Color: Greyed-orange 167A. Pollen — Abundance of shed: High. Pollen germination: Typically greater than 90%. Color: Yellow 11C.

*Self-fruitfulness.*—Low to medium. Planting in field configurations that promote cross fertilization with other southern highbush varieties is recommended for all southern highbush blueberry plants grown in Florida.

Fruit:

*Mean date of* 50% *harvest in Citra, Fla.*—April 10.

*Diameter of calyx aperture on mature berry.*—Mean of 5.3 mm.

*Size and shape of calyx lobes on mature berry.*—Small lobes, semi-erect to erect, straight with slight incurving. Medium calyx basin.

*Pedicel length on ripe berry.*—Mean of 5.3 mm.

*Detachment force for ripe berries* (*easy, medium, hard*) .—Easy.

*Number of berries per cluster.*—Mean of 5.6.

Berry:

*Cluster* (*tight, medium, loose*).—Tight to medium.

*Weight* (*on well-pruned plants*).—Mean of 2.5 g.

*Height.*—Mean of 13.0 mm.

*Width.*—Mean of 17.4 mm.

*Shape.*—Oblate to round.

*Surface color of mature berries ripe on the plant.*—Violet-blue 98D.

*Surface color of ripe berry after polishing.*—Black 203C.

*Immature berry color, with bloom.*—Green 142D.

*Immature berry color without bloom.*—Yellow-green N144A.

*Surface wax.*—Medium to high. The surface wax on 'FL06-203' is persistent and resists abrasion.

*Pedicel scar.*—Small and dry. Mean of 2.4 mm.

*Firmness.*—Very firm.

*Flavor.*—Sweet, low acid, relatively mild flavor.

*Texture.*—Very firm, juicy, small seeds, and no stone cells present.

Seeds:

*Color of dried seeds.*—Greyed-orange 165B.

*Weight of well-developed dried seed.*—Mean of 0.39 mg.

*Length of well-developed dried seed.*—Mean of 1.9 mm.

*Width of well-developed dried seed.*—Mean of 1.1 mm.

Use: 'FL06-203' produces southern highbush blueberries suitable for both the fresh and processed fruit markets. 'FL06-203' has performed best in trials when grown under an evergreen management system.

Resistance to diseases, insects, and mites: 'FL06-203' has grown vigorously and shows medium to good bush survival in the field. It appears to have only average resistance to stem blight (*Botryosphaeria* spp.) and root rot (*Phytophthora cinnamoni*), with some young plants dying soon after planting. Flowers and fruit of 'FL06-203' are particularly susceptible to pre-season *Botrytis* spp. infection, resulting in fruit deformation at the calyx end. Susceptibility to *Botrytis* infection is greater than 'Emerald' (U.S. Plant Pat. No. 12,165) and 'Farthing' (U.S. Plant Pat. No. 19,341), but is controlled with properly timed early-season fungicide applications. The reaction of 'FL06-203' to the fungal species that cause summer leaf spots is typical of other southern highbush varieties, and fungicide applications may be needed after harvest to reduce foliar diseases. 'FL06-203' is moderately susceptible to blueberry gall midge (*Dasineura oxycoccana*).

What is claimed is:

1. A new and distinct southern highbush blueberry plant named 'FL06-203', as illustrated and described herein.

* * * * *